United States Patent
Hamdy (12) 
(10) Patent No.: US 6,261,811 B1
(45) Date of Patent: Jul. 17, 2001

(54) SYNTHESIS OF NATURAL PRODUCT METABOLITES USING IMMOBILIZED FUNGAL SPORES

(75) Inventor: Mostafa K. Hamdy, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 0 days.

(21) Appl. No.: 09/468,564

(22) Filed: Dec. 21, 1999

Related U.S. Application Data
(60) Provisional application No. 60/113,290, filed on Dec. 22, 1998.

(51) Int. Cl.[7] ............... C12P 17/06; C12P 1/02; C12N 11/14; C12N 11/02; C12N 1/14

(52) U.S. Cl. ............ 435/125; 435/41; 435/171; 435/176; 435/177; 435/178; 435/179; 435/180; 435/256.3

(58) Field of Search .............. 435/41, 171, 174, 435/176, 177, 178, 179, 180, 182

(56) References Cited

U.S. PATENT DOCUMENTS 4,929,452   5/1990   Hamdy .................. 426/11

OTHER PUBLICATIONS

Bazaraa et al. "Bioreactor for Continuous Synthesis of Compactin by *Penicillium Cyclopium*", *Journal of Industrial Microbiology & Biotechnology*, 21: 192–202, 1998.

Satoh et al. "Regulation of N–Acetylkanamycin Amidohydrolase in the Idiophase in Kanamycin Fermentation", *Agr. Biol. Chem.*, 40 (1): p. 191, 1976.

Robbers et al. "Physiological Studies on Erogt: Further Studies on the Induction of Alkaloid Synthesis by Tryptophan and Its Inhibition by Phosphate", *Journal of Bacteriology*, 112 (2): p. 791, 1972.

Vliet et al. "Vastatins Have a Distinct Effect on Sterol Synthesis and Progesterone Secretion in Human Granulosa Cells in Vitro", *Biochimica et Biophysica Acta*, 1301: 237–241, 1996.

Bartman et al. "Mycophenolic Acid Production by *Penicillium brevicompactum* on Solid Media", *Applied and Environmental Microbiology*, 41 (3): p. 729, 1981.

Bird et al. "Disposition of Mycophenolic Acid, Brevianamide A, Asperphenamate, and Ergosterol in Solid Cultures of *Penicillium brevicompactum*", *Applied and Environmental Microbiology*, 43 (2): p. 345, 1982.

Gallo et al. "Regulation of Secondary Metabolite Biosynthesis: Catabolite Repression of Phenoxazinone Synthase and Actinomycin Formation by Glucose", *Journal of Bacteriology*, 109 (2): p. 659, 1972.

Goulden et al. "Lysine Control of Alpha–Aminodipic Acid and Penicillin Synthesis in *Penicillium Chrysogenium*", *The Biochemical Journal*, 110: 55p–56p, 1968.

Han et al. "Extended Monod Kinetics for Substrate, Product, and Cell Inhibition", *Biotechnology and Bioengineering*, 32: p. 430, 1988.

Levenspiel, Octave. "The Monod Equation: A Revisit and a Generalization to Product Inhibition Situations", *Biotechnology and Bioengineering*, 22: p. 1671, 1980.

Majumdar et al. "Synthesis of Neomycin by Washed Mycelium of *Streptomyces fradiae* and Some Physiological", *Folia microbiologica*, 16 (4): 285–292, 1971.

Matteo et al. "Production of Gramicidin S Synthetases by *Bacillus brevis* in Continuous Culture", *Journal of General Microbiology*, 96: 415–422, 1976.

Matsuda et al. "Activation of Acyl–Coenzyme A: Cholesterol Acyltransferase Activity by Cholesterol is Not Due to Altered mRNA Levels in HepG2 Cells",*Biochimica et Biophysica Acta*, 1301 (1–2): Abstract, 1996.

Gronroos et al. "Leukotriene D4–Induced Mobilization of Intracellular $Ca^{2+}$ in Epithelial Cells is Critically Dependent on Activiation of the Small GTP–Binding Protein Rho.", *Biochem J.*, 316 (Pt 1): Abstract, 1996.

Alaei et al. "Inhibition of Protein Prenylation Down–Regulates Signalling by Inflammatory Mediators in Human Keratinocytes", *Biochem–Biophys–Res–Commun.*, 222 (1): Abstract, 1996.

Kawabe et al. "Regulation of Fatty Acid Synthase Expression by Cholesterol in Human Cultured Cells", *Biochem–Biophys–Res–Commun.*, 219 (2): Abstract, 1996.

Seronie et al. "Reversion of Transformed Phenotype of Human Adenocarcinoma A549 Cells by Expression of 3–Hydroxy–3–Methylglutaryl Coenzyme A Reductase Complementary DNA", *Cell–Growth–Differ.*, 6 (11): Abstract, 1995.

Shimokawa et al. "Determination of mRNA Levels of Cholesterol Biosynthesis Enzymes and LDL Receptor Using Ribonuclease Protection Assay", *J–Lipid–Res.*, 36 (9): Abstract, 1995.

Lujan et al. "Isoprenylation of Proteins in the Protozoan Giardia Lamblia", *Mol–Biochem–Parasitol.*, 72 (1–2): Abstract, 1995.

(List continued on next page.)

*Primary Examiner*—David M. Naff
(74) *Attorney, Agent, or Firm*—Henry D. Coleman; R. Neil Sudol; William J. Sapone (57) ABSTRACT

Natural product metabolites produced by fungi are synthesized using fungal spores that have been immobilized onto/into a support. Supports that can be used include loofah sponge, synthetic sponge, powdered cellulose paper, wood shavings, calcium alginate gel beads, agar gel beads, channeled aluminum beads, polypropylene beads and glass beads. Immobilizing the fungal spores provides accelerated production of the natural product metabolite in a standard bioreactor. Fungi that can be used include *Penicillium cyclopium, Penicillium chrysogenum, Penicillium citrinum, Trichoderma viride, Aspergillus terreus* and *Monascus ruber*. In a preferred embodiment, spores of *Penicillium cyclopium* NRRL 6233 immobilized with loofah sponge are cultured in a nutrient media for at least 4 days to produce compactin which is a hypocholesteremic agent.

19 Claims, 1 Drawing Sheet

OTHER PUBLICATIONS

Hirata et al. "*Saccharomyces Cerevisiae* YDR1, Which Encodes a Member of the ATP–Binding Cassette (ABC) Superfamily, is Required for Multidrug Resistance", *Curr–Genet.,* 26 (4): Abstract, 1994.

Jingami H. "HMG–CoA Reductase Inhibitor for Therapy of Patients with Hyperlipoproteinemia", *Nippon–Rinsho.,* 52 (12): Abstract, 1994.

Schulz et al. "Prenylated Proteins and Lymphocyte Proliferation: Inhibition by D–Limonene Related Monoterpenes", *Eru–J–Immunol.,* 24 (2): Abstract, 1994.

Endo et al. "HMB–CoA Ped Inhibitors", *Nat–Prod–Rep.,* 10 (6): Abstract, 1993.

Belo et al. "Studies on the Effect of Mevinolin (Lovastatin) and Mevastatin (Compactin) on the Fusion of L6 Myoblasts", *Mol–Cell–Biochem.,* 126 (2): Abstract, 1993.

Gueddari et al. "Evidence for Up–Regulated Low Density Lipoprotein Receptor in Human Lung Adenocarcinoma Cell Line A549", *Biochimie,* 75 (9): Abstract, 1993.

McLeish et al. "Role of Isoprenoid Metabolism in Chemotatic Peptid Receptor–Mediated G Protein Activation", *Biochem–Biophys–Res–Commun.,* 197 (2): Abstract, 1993.

Curdova et al. "Regulation and Biosynthesis of Secondary Metabolites", *Folia microbiologica,* 21: 481–487, 1976.

Norton et al. "Food Bioconversions and Metabolite Production Using Immobilized Cell Technology", *Critical Reviews in Biotechnology,* 14 (2): 193–224, 1994.

Vyas et al. "Stability of a Recombinant Shuttle Plasmid in *Bacillus Subtillis* and *Escherichia Coli.",* *Enzyme–Microb–Technol.,* 16 (3): Abstract, 1994.

Yoshida et al. "Simultaneous Determination of Mevalonate and 7α–Hydroxycholesterol in Human Plasma by Gas Chromatography–mass Spectrometry as Indices of Cholesterol and Bile Acid Biosynthesis", *Journal of Chromatography,* 613: 185–193, 1993.

Kawata et al. "Modulation of the Mevalonate Pathway and Cell Growth by Pravastatin and d–limonene in a Human Hepatoma Cell Line (Hep G2)", *J. Cancer,* 69: 1015–1020, 1994.

Elson et al. "The Chemoprevention of Cancer by Mevalonate–Derived Constituents of Fruits and Vegetables", *Crtical Review,* 607–614, 1994.

Ishihama et al. "Simple and Sensitive Quantitation Method for Mevalonic Acid in Plasma Using Gas Chromatography/Mass Spectrometry", 1994: 377–380.

Giroux et al. "Simvastatin Inhibits the Oxidation of Low–Density Lipoproteins by Activated Human Monocyte–Derived Macrophages", *Biochimica et Biophysica Acta,* 1165: 335–338, 1993.

McCaskill et al. "Procedures for the Isolation and Quantification of the Intermediates of the Mevalonic Acid Pathway", *Analytical Biochemistry,* 215: 142–149, 1993.

Bernini et al. "Requirement for Mevalonate in Acetylated LDL Induction of Cholesterol Esterification in Macrophages", *Atherosclerosis,* 104: 19–26, 1993.

Correll et al. "Identification of Farnesol as the Non–Sterol Derivative of Mevalonic Acid Required for the Accelerated Degradation of 3–Hydroxy–3–Methylglutaryl–Coenzyme A Reductase", *The Journal of Biological Chemistry,* 269 (26): 17390–17393, 1994.*

Plosker et al. "Simvastatin", *Drugs,* 50 (2): 334–363, 1995.*

Correl et al. "Mevalonic Acid–Dependent Degradation of 3j–Hydroxy–3–Methylglutaryl–Coenzyme A Reductase in Vivo and in Vitro", *The Journal of Biological Chemistry,* 269 (1): 633–638, 1994.*

Oda et al. "Effect of Lovastatin on the Cytotoxicity of Ricin, Modeccin, Pseudomonas Toxin, and Diphtheria Toxin in Brefeldin A–Sensitive and –Resistant Cell Lines", *Parental Cell Research,* 212: 329–337, 1994.*

Laaksonen et al. "The Effect of Simvastatin Treatment on Natural Antioxidants in Low–Density Lipoproteins and High–Energy Phosphates and Ubiquinone in Skeletal Muscle", *Am J Cardiol.,* 77: 851–854, 1996.*

Pazzucconi et al. "Therapy with HMG CoA Reductase Inhibitors: Characteristics of the Long–Term Permanence of Hypocholesterolemic Activity", *Atherosclerosis,* 117: 189–198, 1995.*

Drew, Stephen W. "Liquid Culture", *Bacteriology,* American Society for Microbiology: p. 151, 1981.*

Khattak et al. "Utilization of Watermelon Juice", *Food Technology,* 19(6): p. 108–111, 1965.

Khattak et al. "Utilization of Watermelon Juice", *Food Technology,* 19(8): p. 102–104, 1965.

* cited by examiner

FIGURE 1

SYNTHESIS OF NATURAL PRODUCT METABOLITES USING IMMOBILIZED FUNGAL SPORES

RELATED APPLICATIONS

This application derives benefit of priority from provisional application 60/113,290, filed Dec. 22, 1998.

FIELD OF THE INVENTION

The present invention relates to a method for accelerating the synthesis of several or many natural products from fungi and in particular, to the synthesis of natural products using spores which have been immobilized onto/into loofah sponge. It has been unexpectedly discovered that the use of the loofah sponge as an immobilizing support can accomodate the growth of natural product producing fungi from spores at a rate and in an amount which has not been possible before the present invention. The method of the present invention preferably takes place in a standard bioreactor and unepectedly produces large quantities of the desired natural product. In the present invention, the method of using immobilized spores into/onto loofah to synthesize natural products occur for a period of at least about 4–10 days, more preferably about 25 days and even more preferably about 50 days or even longer. In a preferred embodiment of the present invention, spores of *Penicillium cyclopium* which have been immobilized onto/into loofah sponge are used to produce compactin, which is a hypocholesteremic agent.

BACKGROUND OF THE INVENTION

Fungi produce secondary metabolites during growth in response to environmental stress, and these compounds are synthesized from precurors derived from primary metabolites. Many of these products have significant economic value as growth regulators, as antimicrobial agents and as hypocholesterolemic agents. Compactin, a lovastatin analogue, which may be isolated from several fungi, including *Penicillium cyclopium*, functions as a specific competitive inhibitor of the enzyme 3-hydroxy-3-methylglutarylcoenzyme A reductase. Compactin and other compounds, such as simvastatin and pravastatin, have been shown to appreciably lower serum cholesterol levels.

Compactin is an antihypercholesterolemic agent which may affect DNA replication and also may enhance adhesion of tumor cells. Cyclopenol and cyclopenin are also produced by *P. Cyclopium*.

A number of natural products including antibiotics, growth regulators and related pharmaceutical products are produced by isolating natural product (preferably, secondary) metabolites from fungi. The art is therefore always searching for ways to improve productivity and lower costs in providing these products.

It is an object of the invention to provide a method which results in enhanced or accelerated production of natural products from fungal spores.

It is an object of the present invention to provide an immobilization vehicle or platform to produce natural products from spores in submerged or bioreactor systems.

It is an object of the invention to provide a method which results in an enhanced or accelerated production or synthesis of compactin from *Penicillium cyclopium*.

It is a further object of the invention to provide an immobilization vehicle or platform for *Penicillium cyclopium* for use to make compactin in submerged and/or bioreactor systems.

BRIEF DESCRIPTION OF THE INVENTION

The present invention relates to a method for accelerating the synthesis or production of natural products (preferably, secondary metabolites) from fungi using spores immobilized into/onto loofah sponge or a related support. The method of the present invention comprises immobilizing a natural product producing fungal spore into/onto loofah sponge or a related support and then exposing the sponge to nutrient media in a submerged or bioreactor system in order to promote/accelerate the growth of fungi from the spores thereby producing natural product metabolites which may be readily isolated from fermented media in which the fungi has been grown and/or from the fungi. In a preferred embodiment of the pesent invention, a method of making compactin comprises immobilizing spores of *Penillium cyclopium* into/onto loofah sponge or a related support; exposing the immobilized spores to nutrient media containing glucose in a static system or alternatively, at a constant flow rate preferably for a period of at least about 4–10 days, more preferably about 25 days up to 50 days or more; and then isolating compactin from the fungi which grow from the spores and/or the fermented media in which the fungi grow. The method of the present invention may be used in a submerged system or in a standard bioreactor, which has preferably been adapted to accommodate air flow (oxygen) and to enhance the concentration of dissolved oxygen in the nutrient feed stock. Preferably, the method is used in a vertical bioreactor which is adapted to accommodate enhanced air flow and enhanced flow of nutrients in the nutrient media through the system. The combination of increased air (oxygen) flow and nutrient feed stock flow results in greater production of natural product (preferably, compactin) according to the present invention.

In a preferred embodiment of the present invention, the biosynthesis of compactin is conducted by preferably immobilizing the spores into/onto the outer and/or inner layers or small pieces of the outer layer of loofah sponge, which immobilized spores are then suspended in a column to form a bioreactor. The immobilized spores are then exposed to a constant flow of nutrient media and air through the suspended supports within the bioreactor. After a period of time, for example at 6, 8, 12, 16, 24, 48, 72, etc. hour intervals or longer, the media in which the spores are grown is then removed from the bioreactor and replenished with fresh media. The media which is removed from the reactor (otherwise known as "wort" media) contains substantial quantities of the desired natural product. The desired natural product is then isolated from the wort media using standard isolation techniques, including extraction, thin layer chromatography, thick layer chromatography, column chromatography, liquid chromatography, countercurrent distribution and the like and is subsequently and preferably, crystallized to produce the desired product in high purity. In an alternative embodiments used to produce natural products which may accumulate in the fungi, after a period of growth, the fungi which grow from the spores are then harvested, and the metabolites are isolated from the fungi and crystallized to produce the desire natural product.

In the present invention, it is preferred that a bioreactor system be used. The bioreactor may be a continuous-type system where the immobilized spores are exposed to a constant flow of nutrient media and air. Effluent from the bioreactor contains a substantial amount of natural product. This effluent is the wort from which the natural product is isolated. The bioreactor may alternatively be a batch-type (static) system with fungal spores being immobilized into or onto loofah sponge, immersed in nutrient media and exposed to a flow of air. The wort is isolated and natural product separated from the wort at varying intervals in this system. Isolation is similar to that used in the continuous reactor.

DETAILED DESCRIPTION OF THE INVENTION

The term "loofah" or "loofah sponge" is used throughout the specification to describe the fruit of the plant *Luffa aegyptiaca* from the Cucurbitaceae family. It is indigenous to Egypt, but may be found in other parts of the world, including the Southeastern United States. See, R. Muschler, *A Manual Flora of Egypt*, p. 935, S-H Service Agency, 1912, New York, N.Y. In the present invention, the loofah sponge is preferably used as the immobilizing support for fingal spores, particularly, the spores of *Penicillium cyclopium*. While the entire plant of the sponge may be used, it is preferred that the core of the sponge should be removed and the outer layer used for immobilization. It unexpectedly has been found that the structure of the sponge provides a particularly suitable environment for the immobilization of fungal spores of natural product producing fungi for use in submerged or bioreactor systems. The amount of loofah which may be used is that amount effective to support the rapid growth of fimgi within the growth system used (bioreactor or submerged growth system) and which will allow nutrients to readily pass through and bath the spores which are attached to the loofah.

The term "support", "related support" or "immobilizing support" is used throughout the specification to describe a a support or immobilizing support, including loofah sponge, described above into and/or onto which fungal spores are adsorbed and/or entrapped, which is used to significantly enhance production (i.e., at least 1.5 times, preferably at least two times and more preferably at least 5 about times the amount produced in a given time period using prior art methods) of a natural product using the methods generally described in the present invention. Materials other than loufa sponge which may be used as support for use in the present invention include, for example, synthetic sponge material having average pore sizes preferably ranging from about 0.01 mm to about 5 mm in diameter, powdered cellulose paper (preferably, having a specific mesh size ranging from about 20 to 100, preferably about 10 to 25, more preferably about 16 to 20); wood shavings (preferably, cherry or oak wood shavings being at least about 0.5 inches in length, preferably about 1 to 4 inches in length, even more preferably about 3 inches in length and preferably about 0.5 to 10 mm thick, more preferably about 2 to 5 mm thick); calcium alginate gel beads (prepared from alginic acid/alginate in which fungal spores have been mixed, placed in aqueous solution and precipitated with a calcium salt, for example, calcium chloride) having gel bead diameters preferably ranging from about 2–5 mm; agar gel beads (prepared from agar mixed with spores at about 50° C. and then placed in cold water to form a gel); chanelled aluminum beads (preferably type E beads having pores with an average diameter ranging from about 2.5 to 12 $\mu$m ($10^{-6}$ meter); Porex beads (plastic beads, preferably polypropylene beads available from Porex Technologies, Inc., Fairbum, Ga., USA, preferably ranging in size from about 50 $\mu$m to about 5 mm (preferably, about 2 mm to 5 mm) in diamater and having pore sizes preferably ranging from about 5–30 $\mu$m and glass beads ranging in size from about 2.5 to about 12 $\mu$m. All of the above-described immobilizing supports produce natural products in amounts which are significantly enhanced compared to prior art methods of production. This is an unexpected result.

The term "natural product producing spore" or "mold spore" is used to describe a fungal spore which can be used in the present invention to produce natural product. Generally, the spore produces natural product throughout its life from the free spore stage through the formation of hyphae and mycelia. The spore typically attaches to a sedentary object or platform (solid support) and matures into a fungus. The fungus is a spore or is spore-like at an early stage of growth or development, and as the organism matures, it contains branch-like. mycelia. Generally, at each stage of growth, i.e., at the spore stage, an early growth stage where the organism comprises primarily hyphae or at a later stage of growth where the organism comprises densely growing mycelia, the organism produces a desired natural product which can be isolated. The spores according to the present invention are those which produce antibiotics, antifungal agents, growth regulators and related natural products. Any spore which, as part of its growth process, attaches to a sedentary object in order to promote growth may be advantageously immobilized and used in the present invention. Exemplary fungi include, for example antibiotic producing fungi such as *Penicillium chrysogenum, Penicillium citrinum, Trichoderma viride, Aspergillus terreus* and *Monascus ruber*, among numerous others. It has unexpectedly been discovered that the loofah sponge or a related support as otherwise described herein, provides a particularly advantageous immobilization medium or platform for virtually all natural product producing spores which attach to a sedentary object or platform for growth. The use of loofah sponge is clearly preferred for use in the present invention. While not being limited by way of theory, this appears to be due to the favorable three-dimensional structure which can accommodate the growth of the fungi and the efficient flow of nutrients to the fungi, and to the stability of the sponge to sterilization and to hydrolysis in nutrient media which is used to grow spores and fungi. Particularly preferred spores for use in the present invention include compactin producing spores of the species *Penicillium cyclopium*, which are preferably hyperproducers of compactin. A particularly preferred strain of *Penicillium cyclopium* is NRRL 6233, which is available from the U.S. Department of Agriculture, Northern Regional Research Laboratory, 1815 North University, in Peoria, Ill., USA 61604 (Tel 309-685-4011). The strain was originally deposited on Apr. 29, 1976 and its viability was tested no later than May 29, 1976. It is most preferably used as an aberrant (stressed) organism.

The term "immobilized" is used to describe loofah sponge onto and/or into which spores of natural product producing fungi, preferably, *Penicillium cyclopium* have attached (are adsorbed and/or entrapped) and are growing. During the process of immobilization, the spores attach themselves to the sponge in a manner which will afford growth. This is a natural process by which spores normally affix themsevles to a sedentary object, during the natural growth processes. In the present process, spores are allowed to grow in medium in conjunction with the loofah sponge or a related support. Naturally, the spores will affix themselves to the support in order to promote growth. It has been found that the loofah sponge is a particularly advantageous immobilization platform because the microscopic three-dimensional structure of the sponge is such that after immobilization, the growth of spores into more mature fungi can be readily accommodated. It is surprising that the spores may grow steadily for many days (even in excess of 50 days) immobilized on the loofah sponge without being inhibited from further growth. This represents an unexpected result.

Spores become immobilized into/onto the sponge by inoculating sterile sponge material (whole or pieces) or related immobilizing support with effective concentrations of spores (conidiospores) in th presence of nutrient media. The concentration of spores which are used for immobilization may vary greatly depending upon the species of fungi used, but in general, effective concentrations of spores for inoculation may range from about $1 \times 10^6$ to $5 \times 10^9$ per ml or higher (i.e., more concentrated), with preferred concentrations varying within this ratio depending upon the growth phase of the spores and the rate at which the fungi grow. In a preferred embodiment, the number of spores of *Penicillium cyclopium* used as an inoculate falls within the range of about $1 \times 10^8$ spores to about $5 \times 10^9$ spores per ml, with a preferred concentration being about 1 billion ($1 \times 10^9$) spores per ml. Generally, the same nutrient medium which is used to grow the spores after immobilization is used for inoculation/immobilization. After inoculation, the immobilizing support (preferably, loofah sponge) and spores are incubated in the presence of nutrient medium for a period of a few hours to 5 days or more, before being added to the bioreactor or submerged culture for growth. In the case of *Penicillium cyclopium*, incubation after inoculation is preferably conducted for a period of about 24 hours. The temperature of inoculation/immobilization is preferably the same as the temperature for growing the spores in the bioreactor and is preferably about 20–30° C., more preferably about 22–27° C., even more preferably about 25° C.

Most of the spores useful in the present invention exist as free spores, which are preferred for use in the present invention. However, spores which are in different growth phases may also be used in the present invention. Thus, spores which have been allowed to grow a short period (in the case of *Penicillium cyclopium*, about 36 hours) and are in the trophophase or spores which have been allowed to grow a bit longer (in the case of *Penicillium cyclopium*, about 106 hours) and are in the idiophase may also be used in the present invention.

The term "natural product" is used to describe any one or more of various chemical products which are produced as metabolites (preferably, secondary metabolites) during growth of the fungi which grow from spores according to the present invention. Depending upon the species of fungi, these natural products may be antibiotics, growth regulators, and related pharmacological or biological products.

The term "compactin" is used to describe 2-methyl-8-(2-methyl-1-oxobutoxy)-mevinic acid lactone, the antihypercholestermic compound which is produced by *Penicillium cyclopium*, more preferably a hyperproducer of compactin such as *Penicillium cyclopium* NRRL 6233 (available from the Department of Agriculture, Peoria, Ill., USA). Also known as ML-236B, this compound is a competitive inhibitor of the enzyme 3-hydroxy-3-methyl glutaryl-co-enzyme A reductaste (HMG-CoA reductase E.C. 1.1.1.34).

The term "bioreactor" is used throughout the specification to describe a batch or continuous-type reactor which is adapted to grow organisims and in turn, to produce natural products from the organisims which are grown in the bioreactor. In the present invention, a bioreactor may be advantageously used for the continuous synthesis of natural products, one of which, compactin, may be isolated from *Penicillium cyclopium*. In general terms, as used herein, a bioreactor may be any system adapted to allow rapid growth of a fungal spore using an immobilized microorganism exposed to a constant flow of nutrients, thus producing a rapid or maximum growth of the desired organism. Bioreactors are preferably made from an inert material such as stainless steel or preferably glass. An exemplary bioreactor may comprise a vertical Pyrex (glass) column which is adapted with at least two inlets for medium and air at the bottom of the column and at least one outlet port at the top of the column to accommodate expunged medium and/or air. In the present invention, the bioreactor is preferably adapted with inlets at the bottom of the bioreactor to allow air and media to be placed into the system. Preferably, the air inlet is adapted to allow filtered air (preferably, sterilized) to bubble into the medium in which the organisms is growing in the bioreactor. At or near the top of the bioreactor is preferably one outlet, an outlet which allows air to flow out of the bioreactor and the which also allows spent media (wort) to be removed from the system. A particularly useful bioreactor which may be easily modified as described above and used in the present invention is that described in U.S. Pat. No. 4,929,452, issued May 29, 1990, relevant portions of which are incorporated by reference herein. See also, Hamdy, et al., *Biomass*, 21, 189–206 (1990), which also may be used as a guide for purposes of providing bioreactors which are useful in practicing the present invention.

The term "submerged system" is used to describe a growth system which may also be used in the present invention. A submerged system refers to any growth system in which the immobilized fungi of the present invention may be submerged under nutrient media for growth. An exemplary submerged system may include the use of fermentation vessels containing the immobilizing support (preferably, loofah sponge) with the immobilized spores. The vessels are equipped with air nozzles or air spargers for delivery of air through the media in the system. Any system which is useful to submerge the immobilized spores in nutrient media and which can accommodate the delivery of air through the media may be used in the present invention.

The term "nutrient medium" or "nutrient media" is used throughout the specification to describe growth media which is used to grow spores according to the present invention. At its minimum, growth medium according to the present invention is at least a minimum essential medium with added glucose. Such medium comprises the following elements: (a) essential amino acids; (b) non-essential amino acids; (c) vitamins; (d) a mixture of inorganic ions and (e) glucose. All of these elements (a), (b), (c), (d) and (e) are included within a minimun essential nutrient medium for growth of fungi. All of the above elements are included in the nutrient media in concentrations and/or amounts effective for enhancing the growth of the spores and fungi of the present invention. Each of the above elements may be varied pursuant to routine experimentation in order to produce a medium which provides optimum results of growth and production of the desired metabolite (natural product). Media which contain amino acids or small digestible peptides (for example, which would be available from a peptone product) and which include glucose and a buffer (in order to maintain the pH of the media within an optimal range) are clearly preferred. One of ordinary skill may readily vary the componentry of the nutrient media which may be used in the present invention in order to provide metabolites from the growth of spores according to the present method.

Preferred media for use in the present invention include, for example, media which is prepared from malt and peptone, which further includes glucose and a buffer, preferably citrate or succinate buffer. Preferred media for use with *Penicillium cyclopium* includes malt glucose peptone broth (MGPB, Endo, et al., *J. Antibiot.*, 29, 1346–1348 (1976)); and glucose basal salt broth (GBSB, Schröder, P., *Biochem. Physiol. Pflanzen*, 172, 161–166 (1978)), with MGPB containing glucose and citrate as a buffer clearly preferred. Numerous nutrient media, which contain above basic components, using, for example, yeast extract, mycological broth and related nutrients may also be used in the present invention. One of ordinary skill in the art may choose the appropriate nutrient media and the literature is replete with exemplary media which contain the above basic components and can be used in the present invention. MGPB media to which has been added sodium citrate is particularly preferred for use with *Penicillium cyclopium* in the production of compactin according to the present invention. The concentration of glucose may vary, but generally will fall within the range of about 0.01% to about 2.5% by weight, more preferably about 0.1% to about 1% by weight, more preferably about 0.5% to about 1% by weight of the nutrient media.

The term "wort media" or "wort fermented media" is used to describe media containing natural product metabolites in which spores (fungi) have been grown.

The pH of the nutrient media may range broadly from about 3.0 to about 8.5 or higher, depending upon the fungal spores to be used, but, in the case of *Penicillium cyclopium*, the preferred pH ranges from about 4.0 to about 5.5, with a preferred pH of about 4.0. By buffering the pH appropriately, maintenance of a particular pH value within a relatively narrow range will readily occur.

The inclusion of glucose and a buffer (preferably, a citrate or succinate buffer) within the media is preferred. Glucose has been shown to provide greater production of primary metabolites and a lesser amount of secondary metabolites, a condition which is preferred. The inclusion of about 0.01% to about 2.5% by weight of glucose or more in the nutrient media will result in greater metabolite, especially compactin synthesis. A more preferred weight range of glucose in the nutrient media is about 0.2% to about 1% by weight, even more preferably about 1% by weight. The use of complex carbohydrates which hydrolyze into glucose is also contemplated by the present invention, although in the case of the use of certain dissccharides, such as sucrose, which hydrolyzes to produce glucose and fructose, this is less preferred, presumably because the production of fructose appears to have an inhibitory impact on the ultimate production of certain metabolites, especially compactin.

The amount of buffer which is included within the nutrient media is that amount which is effective to maintain the pH within a range of about ±0.3 pH units, preferably within a range of about ±0.1 pH unit. The concentration of buffer included within the nutrient medium according to the present invention ranges from about 0.01M to about 0.5 M, with a preferred concentration range being about 0.05M to about 0.15 M, most preferably about 0.1M. Citrate buffer (from, for example, sodium or potassium citrate, more preferably sodium citrate) or succinate buffer (from, for example, sodium or potassium succinate).

The temperature at which the spores/fungi are grown in the present invention may varying depending upon the species of fungi used, the temperature which produces optimal growth and production of the desired natural product metabolite. This temperature may range from about 20° C. to about 30° C., more preferably about 23–25° C.

In the methods according to the present invention, the amount of air which flows through the system is an important consideration for determining the amount of metabolite produced. In the case of fungal spores, which rely on aerobic metabolism, air (oxygen) is an important component to be added to the system in order to maximize production of the desired metabolite.

The flow rate of air through the system will determine the amount of dissolved oxygen in the nutrient media. The rate of delivery of air to the system which is preferred will vary in each case, depending upon numerous factors including: the type of organism and nutrient media used, the dimensions of the bioreactor, the temperature of the system, and the amount of loofah sponge used to immobilize the spores (density of the packing of the sponge). In general, it is preferred that the amount of air to be added to the system is that amount which produces the greatest production of metabolite in combination with the other factors. Thus, the amount of air may be adjusted accordingly and may vary over a significant range. However, the amount of air chosen is that amount which tends to increase the dissolved oxygen within the media in order to increase the metabolism by the fungi in producing the desired natural product metabolites. As a general rule, one may have to experiment to optimize the air flow within the growth system (submerged or bioreactor) used, but this is considered to be well within the skill of those in the art. In the case of compactin production using *Pencillium cyclopium*, the amount of air which is added to the submerged or bioreactor system preferably ranges from about 0.5 volume of air per volume of nutrient media per minute to no greater than about 3 volumes of air per volume of nutrient media per minute, more preferably about 1 to 2 volumes of air per volume of nutrient media per minute. In general, although the amount of air added to the system may vary, as a guiding principle, the amount of air to be added to the system preferably will be that which produces high concentrations of dissolved oxygen, including maximal concentrations of oxygen within the system. In general, filtered (sterile) air is added to the system in order to avoid microbial contamination.

The rate of flow of nutrient media (which may alternatively be described in terms of a dilution rate) within the continuous bioreactor system may vary over a fairly wide range, but is chosen to maximize growth of fungi and production of natural product within the system. The rate of flow is generally defined in terms of a volume flow of nutrient media per hour. Flow rates of approximately 7.8 to 90 ml per hour (ml h$^{-1}$), corresponding to a dilution rate of 0.12 to about 1.35 h$^{-1}$, may be used preferably within the present invention for maximizing the production of compactin. In the case of the production of other natural products, the flow rate and dilution rate may well fall outside of this ratio, depending upon a number of factors. One of ordinary skill may readily adjust the flow rate, and consequently the dilution rate within the teachings of the present invention in order to provide a maximal flow rate for producing a natural product according to the present invention.

In the present method, after immobilized spores are exposed to nutrient media, the media is collected and the desired metabolites are then isolated from the used media (wort). In certain instances, depending upon the fungi used to synthesize the desired natural product metabolite, it may be necessary for complete harvest to collect the fungi and isolate some of the metabolite from the cells. However, in most instances, the fungi secrete the desired metabolite into the used nutrient media (wort), from which the media will be isolated without collecting the fungi. This is the case with the synthesis of compactin from *Penicillium cyclopium*.

Isolation of the desired natural product from the wort nutrient media will generally involve a sequence of steps which may first include a homogenization step followed by one or more extraction steps. The solvent used for homogenization and extraction may vary over a wide range depending upon the polarity of the natural product to be isolated from the media. In the case of the homogenization solvent, this generally includes a solvent which is miscible with water, for example, acetone, ethanol or other water-miscible solvent.

After the homogenization step and evaporation of solvent, the remains are generally extracted with a solvent such as ethyl alcohol, ethyl acetate or another somewhat polar solvent in order to assure that most, if not all of the desired metabolite is extracted from other components in the nutrient media. Of course, it is to be understood that the type of solvent used in the extraction step(s) may vary greatly depending upon the polarity of the metabolite to be isolated. More polar (hydrophilic) metabolites will require the use of more polar extraction solvents such as ethanol, ethyl acetate or acetone, and less polar (hydrophobic) metabolites will be more efficiently extracted with more hydrophobic solvents such as ether, methylene chloride, aromatic hydrocarbons and related solvents.

After the extraction step, the resulting extract containing the desired natural product is dissolved in an appropriate solvent for performing a separation step, which generally involves the use of chromatography (thick layer, column or liquid) or countercurrent distribution. Standard silica gel column chromatography may be used, or alternatively, techniques which provide even greater resolution such as the use of high pressure liquid chromatography or high performance thin layer chromatography may be used. After separation, the contents of the fractions which result from the chromatography are combined and the natural product contained in the combined fractions is crystallized/recrystallized to purity.

Figure 1:
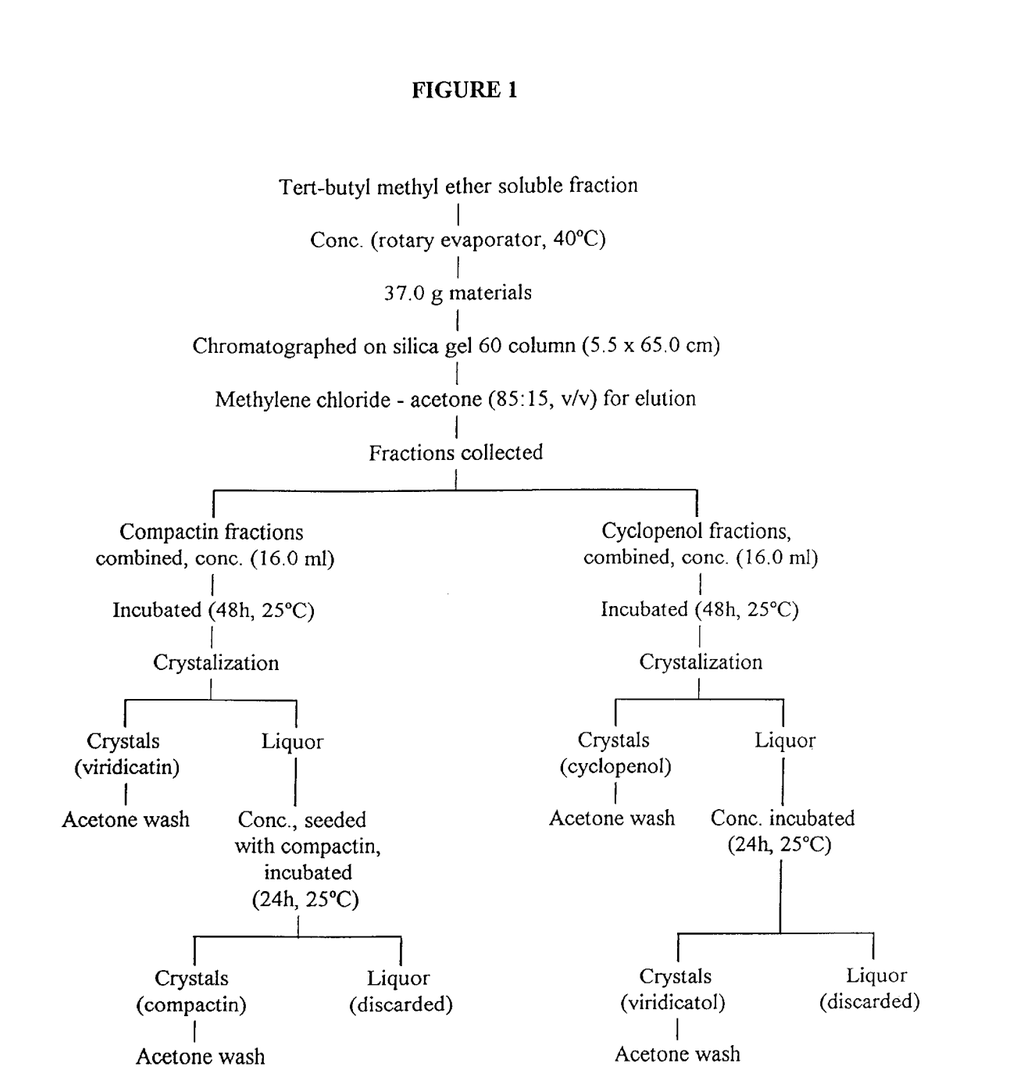
FIG. 1 is a schematic diagram showing isolation and purification of compactin.

In the case of the isolation of compactin from wort media, the following exemplary method may be used. The wort media is first homogenized with acetone, the acetone evaporated from the homogenized media and the pH of the remaining material is adjusted to approximately 4.0 and then extracted with ethyl acetate. The combined extracts were concentrated at 40° C. under vaccuum, taken up in solvent and applied to a silican gel column. The column is sequentially eluted first with a non-polar solvent such an aromatic hydrocarbon (benzene, toluene and the like) and is then eluted with progressively more polar solvents such as tert-butyl methyl ether, ethyl aceate, acetone and acetonitrile. The fractions containing compactin, in the above-described case, the tert-butyl methyl ether fractions, are concentrated and then subjected to the method which is set forth in attached FIG. 1, which includes the use of at least one additional column chromatography step in order to separate the compactin from related metabolic components in the sample.

In the case of the isolation of other natural product metabolites pursuant to the present invention, one of ordinary skill may readily modify the above teachings and use standard isolation techniques to isolate virtually any natural product pursuant to the present invention.

In its broadest aspect, the present invention relates to a method of synthesizing a natural product from fingi comprising:

1) immobilizing spores of said flngi into or onto an immobilizing support, most preferably loofah sponge, to produce immobilized spores;
2) exposing said immobilized spores from step 1) to nutrient media in a submerged or bioreactor system for a period of at least 5–10 days to produce a natural product metabolite of said fungi in nutrient media which has been collected from said system (wort media); and
3) isolating said natural product from said media.

Preferred embodiments of the above-described general method may be readily gleaned from the preceding detailed description of the invention and the examples which follow. Having generally described the invention, reference is now made to the following examples which are intended to illustrate preferred embodiments and comparisons but which are not to be construed as limiting to the scope of this invention as is more broadly set forth above and in the appended claims.

EXAMPLES

Materials and Methods

The following materials, reagents and media were used in the examples. Oxoid potato dextrose agar (Basingstoke, Hants, England); Nabisco shredded wheat (East Hanover, N.J.); loofah sponge (local market); silica gel 60F-254 plates (Merck, Darmstadt, Germany); compactin from Dr. Chu, (Col. Pharm., UGA, Athens, Ga.) cyclopenol, cyclopenin and viridicatin from Dr. Cutler, (Plant Physiol., USDA, Athens, Ga.). All chemicals were of reagent grade and with highest purity available. Anisaldehyde reagent consisted of: methanol, 85 ml; concentrated sulfiuc acid, 5 ml; and p-anisaldehyde, 0.5 ml, see Wagner, et al., "Plant Drug Analysis, A Thin Layer chromatography atlas". p299 Springer-Verlag, Berlin Heidelberg, New York.; Párducz solution was prepared by mixing osmium tetraoxide (4%, w/v) with water and saturated mercuric chloride solution using 3:3:1, v/v ratio, respectively; anthrone reagent had 0.2 g anthrone in concentrated sulfuric acid and water mixture (95:5, v/v ratio). Semisolid medium was described by Cutler et al., *Plant and Cell Physiol.*, 25, 257–263 (1984) and Doss et al., *J. Nat. Prod.*, 49, 357–358 (1986) and contained (g $l^{-1}$ distilled water, DW): mycological broth (pH 4.8), 50; yeast extract, 20; and sucrose, 200. Two hundred ml of this broth was added to 100 g shredded wheat in Fernbach flasks (2.8 liters) and sterilized (45 min, 121° C.). Three types of liquid media were also used: MGPB [Endo, et al., *J. Antibiot.*, 29, 1346–1348 (1976)]; glucose basal salt broth (GBSB) of Schr öder [*Biochem. Physiol. Pflanzen*, 172, 161–166 (1978)]; and sucrose yeast extract mycological broth (SYEMB) of Cutler et al., supra. The liquid media had (g $l^{-1}$ DW) for each: MGPB—malt extract, 30; glucose, 20; and peptone, 1.GBSB—glucose, 100; sodium citrate 38.2; $NH_4Cl$, 3.8; $CaCl_2.2H_2O$, 2.1; $MgSO_4.7H_2O$, 0.15; $KH_2PO_4$ 0.13; KCI, 0.05; FeSO4.7 $H_2O$, 0.05; $ZnSO_4.7H_2O$, 0.02; the glucose and $MgSO_4$ were sterilized separately and added to the medium before inoculation: SYEMB—sucrose, 200; mycological broth, 50; and yeast extract, 20. All media, unless otherwise stated, were adjusted to pH 5.5 and sterile anti-foam (poly-propylene gylcol, MW 2000) was added to media (0.0125%) prior to inoculation.

Culture and Conidospores

An aberrant (stressed) *P. cyclopium* strain [NRRL 6233], supplied by Dr. Cutler (USDA, Athens, Ga.), was maintained on potato dextrose agar slants (Difco, MI) and used to inoculate several (200 ml each) Difco mycological agar slants (pH 4.8) for seven days incubation (25° C.). The conidiospores were harvested using sterile DW, combined, mixed well, microscopically counted ($3.0\times10^9$ spores $ml^{-1}$), stored at 4° C. and used as inoculum when needed. NRRL 6233, is available from the U.S. Department of Agriculture, Northern Regional Research Laboratory, 1815 North University, in Peoria, Ill., USA 61604 (Tel 309-685-4011). The strain was originally deposited on Apr. 29, 1976 and the viability of the strain was tested no later than May 29, 1976. Samples may be obtained by writing to the United States Department of Agriculture at the above address or telephoning them at the above number. The strain is made available by the Department of Agriculture to the public in perpetuity and the sample is monitored for viability. Otherwise see, for example, Cutler et al., *Plant and Cell Physiol.*, 25, 257–263 (1984).

Submerged Culture

Fermentation vessels (1.8 liters each) containing the desired media were used and each vessel, equipped with an air sparger which supplied 1.2 liters sterile (filtered) air/1.2 liters media $min^{-1}$ (v/v $min^{-1}$), was inoculated and incubated (25° C.). At intervals, cell-mass was monitored by withdrawing 60 ml from each vessel, filtering through preweighed Whatman No. 4 filter paper, washing the cells with deionized water, drying under vacuum (80° C.) and weighing. The filtrate was also assayed for pH, the concentration of reducing sugars, total carbohydrate, compactin and other metabolites. The following factors affecting the submerged culture system were examined: air flow into sparger [0.5,2.0, and 3.0, v (air)/v (media) $min^{-1}$)], glucose level, 0.0,0.5, and 1.0%); pH ofbuffered [4.0 and 5.5 citrate (0.1 M) were added to yield the desired pH] and unbuffered MGPB (4.0,5.5, or 7.0 and pH adjusted before sterilization); buffer type, acetate, citrate or succinate added to MGPB (pH 4.0, 0.1 M); buffer molarity in MGPB using different (M) citrate levels (0.01, 0.05, or 0.10 M) adjusted to pH 4.0.

Isolation and Purification of Metabolites

A total of 54 Fernback flasks, each containing the semi-solid media (mycological broth with shredded wheat), were (each) inoculated and incubated for 14 days (25° C.). The content of each flask was then homogenized with 300 ml acetone for 3 min in explosion proof homogenizer, the homogenate filtered and filtrates combined, the acetone evaporated (40° C.), the pH adjusted to 4.0 and then again extracted twice using equal volumes of ethyl acetate. The combined extracts were dried over anhydrous $Na_2SO_4$, concentrated (40° C.) to ≈250 ml viscous material. Aliquots were chromatographically assayed (TLC) using silica gel 60 F-254 plates (5×10 cm) and methylene-chloride-acetone mixture (85:15, v/v ratio) as the developing solvent. Five pure standards, compactin, cyclopenol, viridicatin, cyclopenin and viridicatol, were used for comparison on TLC plates and viewed under UV-254 nm or after two min heating following spraying with the anisaldehyde reagent. The viscous concentrated extract (130 ml was also fractionated on silica gel 60 (70–230 mesh) prep-column (9.0×23.0 cm) and consecutively eluted using one liter each of the following solvents: benzene, tert-butyl methyl ether, ethyl acetate, acetone and acetonitrile. Aliquots of each solvent fraction were concentrated and assayed on the TLC plates as previously described. The tert-butyl methyl ether soluble fraction containing the metabolites was concentrated (40° C.) and subjected to the following separation and purification procedure to ensure compactin isolation from other metabolites: 37 g of this fraction was applied to a 2nd silica gel 60 (70–230 mesh) column (5.5×65.0 cm) and eluted using methylene chloride-acetone mixture (85:15, v/v ratio fol-lowing the schematic diagram shown in FIG. 1. Ten ml fractions were collected using a fraction collector. Those containing compactin were combined, concentrated to ≈16 ml kept for two days (25° C.) to form crystals which were removed from the mother liquor, washed twice with acetone, air dried and again subjected to TLC analyses. The solvent fractions containing other metabolites were treated similarly.

The isolated compactin was also subjected to proton nuclear magnetic resonance analyses ($^1$HNMR), compared to standard (98.0% pure) and percent purity determined. The spectra were recorded (20° C.) on a Jeol FX90Q Fourier Transform 90 MHZ $^1$HNMR spectrometer (Tokyo, Japan) using specified acquisition conditions. The isolated and purified compound ($R_f$ value 0.09) was subjected to low resolution electron impact mass spectral analyses using a Hewlett Packard 5985 spectrometer (Palo Alto, Calif.), introduced by a direct insertion probe following specified conditions and the resulting spectrum compared with reference library standards for compounds with the same structure and molecular weight.

Metabolites and Assays

Solubilities and UV spectra of each isolated metabolite, in different solvents (acetonitrile, methanol and/or hexane), were examined using a Hewlett Packard 8451A diode array spectrophometer (Palo Alto, Calif.). The concentrations of metabolites in fermented liquid media (wort) were also determined as follows: 60 ml wort, filtered, filtrate adjusted to pH 4.0 placed in a separatory funnel, and extracted twice (each for four min) using equal volumes of ethyl acetate. The ethyl acetate phases were combined, dried, again extracted with 1.0 ml acetonitrile, centrifuged for three min (12,000× g), the supernatant diluted and scanned at 200 to 330 nm. When compactin and/or cyclopenol were present, the absorbance at 238 and/or 286 nm was then determined. If cyclopenin was present in the semisolid shredded wheat media (SWM), a modified process was used to separate cyclopenin from compactin using two directional high performance thin layer chromatography [HPTLC, Dixon, et al., *J. Rapid methods*, 4, 251–263 (1996), on silica gel 60F-254 plates (10×10 cm). Benzene-acetone-acetic acid mixture was utilized as the first solvent (50:50:3, v/v ratio) followed by methylene chloride-acetone mixture (85:15, v/v ratio) for the 2nd direction. Specific areas (on plates) corresponding to compactin and/or cyclopenol standards were scraped, collected, pulverized, and extracting the solid fines twice with 1.0 ml acetonitrile. The extracts were combined, centrifuged, supernatant diluted and assayed using the above HPTLC system. Percent recovery of compactin from the TLC plates was also determined using known concentrations of this metabolite and following the same analysis procedure.

Immobilization

Loofah sponge, used as the carrier support for the fungus, was soaked in deionized water for ten min, the core removed and the outer layer sliced into cubes (≈1.0×1.0×1.5 cm). After sterilization (121° C., 15 psi, 15 min), the cubes were soaked in sterile SYEMB for one h. Several cubes were transferred to sterile petri dishes (15.0×2.5 cm), inoculated with the conidiospores-suspension, incubated (25° C.) to desired growth phase and then transferred to fermentation flasks or to the bioreactor column. Factors affecting syntheses in batch system were examined and included growth phase (age) of inoculum used for immobilization, loofah concentration and incubation time. The flasks containing 60.0 ml modified (A) MGPB as well as a specified amount loofah cubes were inoculated, and incubated in a shaker water bath (130 reciprocating $min^{-1}$, 25° C.). The (A)

MGPB had citrate and less glucose than the original MGPB (0.5% glucose and 0.01 M citrate, pH 4.0). Three growth phases of inoculum were utilized and compared for compactin syntheses as a function of incubation time: the 1st phase was a conidiospore suspension (0.3 ml containing $1 \times 10^9$ spores $ml^{-1}$) directly added to the loofah cubes at zero time in the flasks; the 2nd and 3rd phases, the spores (same numbers) were inoculated, allowed to grow for 36 h (trophophase) and/or 106 h (idiophase), respectively. Each phase was used for immobilization to loofah with the desired media. Free (not immobilized) spore suspensions were utilized as controls and treated similarly. Assays of cell-mass, pH, reducing sugars, and metabolites were conducted at intervals during each experiment. Several different amounts of loofah (0.1, 0.3, 0.6, 0.9, and 1.5 g dry wt) were each added to flasks containing 60.0 ml modified (A) MGPB. After inoculation, the flasks were incubated in a shaker water bath (130 reciprocating $min^{-1}$, 25° C.) for 12 days and compactin level as well as cell-mass determined. The specific compactin concentration was ascertained and reported as compactin (mg)/total cell-mass of loofah (g).

Bioreactor System

Two vertical Pyrex columns [No. I (27.0×3.3 cm) and No. II (44.5×7.5 cm)], each with two (bottom) inlets (air and media) and one (top) outlet (exit port), were used [Hamdy, et al., *Biomass*. 21, 189–206 (1990)]. Columns and rubber connectors were sterilized by immersion in ethanol 70% (v/v) for 24 h, and the other components were autoclaved for 45 min at 121° C. The total volume of each column (I & II) were 0.28 and 1.75 liters with void volume of 0.24 and 1.6 liters, respectively. Column No. I was packed with the loofah cubes (3.5 g dry weight) and column II had the entire (whole) loofah. The immobilization was conducted as follows: six cylindrical loofah cubes (6.5×6.0 cm) or the entire loofah, were placed in a two liter covered beaker, sterilized, growth media inoculated, incubated (24 h at 25° C.) and then aseptically transferred to the column. Each column (I and/or II) containing the immobilized-cell-loofah-preparation was fed with modified (B) MGPB as feedstock (FS). This media had (g $l^{-1}$ DW): malt extract, 30; glucose, 5; peptone, 1; and citric acid, 1.92 at desired pH. Unless specified, sterile air was supplied to each column at 30 ml $min^{-1}$ during fermentation, the system was operated in batch mode until the compactin level reached the steady state. This was followed by continuous mode at which time the effect of dilution rate [$d^{-1}$=flow rate (ml $d^{-1}$/reactor void volume (ml)] was examined. The effluents were collected at intervals, assayed for compactin levels formed ($\mu g$ $ml^{-1}$) and productivity (mg $l^{-1}$ $d^{-1}$) and residual reducing sugars.

Scanning Electron Microscopy (SEM)

This was used to evaluate the loofah ultrastructure, examine the attachment of *P. cyclopium* conidiospores onto-into the loofah fibers and the growth characteristics of the mold post-immobilization. Loofah specimens were fixed (3 min) in an ice bath using the Pârducz, *Int. Rev. Cytol.*, 21, 91–98 (1967) procedure, following specified conditions, mounted on aluminum stubs with silver paint and coated with 400 Å, & mixture of gold-palladium (6:4, w/w ratio) in a Hummer Sputter Coater Alexandria, Va.) and viewed at 20.0 KeV using SEM Philips 505.

Media Analyses and Statistics

Total reducing sugars were assayed following the Bemfeld procedure [Bemfeld, P., *Methods in Enzymology* p. 149, Colowick and Kaplan, eds. Academic Press, New York, 1955], total carbohydrate by anthrone reagent [Viles, et al. *Anal. Chem.* 21, 950–953 (1949)] and Monod [Monad, *Annual Review in Microbiology*, p. 371–394, annual Reviews, Stanford 1949] for growth kinetics based on Michaelis-Menten expression. The Monod constant was calculated from batch system data by fitting the linearized model expression to the data of average-substrate weight and cell-mass. Data were subjected to one-way analyses of variance [Ramachandran, et al., *Cancer. Res.*, 46, 2520 (1986)] and unless otherwise stated, averages reported were the result of three experiments.

RESULTS AND DISCUSSION

The crude extract of SWM, after 14 days growth of *P. cyclopium*, contained seven secondary metabolites on TLC plates. Sequential solvent fractions on silica gel prep-column of the crude extract contained different metabolites in each fraction; the benzene soluble fraction had the unidentified compound (A); the tert-butyl methyl ether soluble fraction exhibited the seven metabolites; the ethyl acetate fraction had five, but none of the unidentified compounds; the acetone-soluble fraction had viridicatol, and the acetonitrile fraction yielded none. Since the seven metabolites were in the tert-butyl methyl ether soluble fraction, fuirther isolation-purification of each metabolite was employed using a large silica gel column from which 10.0 ml fractions were collected. Fractions Nos. 55 to 110 (550 ml total had the unidentified metabolite (A); cyclopenin was in Nos. 135 to 205; compactin in Nos. 165 to 350; viridicatin detected with compactin in fractions Nos. 165 to 250; cyclopenol in Nos. 420 to 650 and viridicatol in Nos. 470 to 650. The fraction containing compactin and viridicatin (Nos. 165 to 350) were combined, concentrated to ~16.0 ml, and kept for two days at 24° C. to form viridicatin crystals. The resulting mother liquor was again concentrated, then seeded with pure compactin, yielding the purified compactin crystal. Fractions Nos. 420 to 620 were also combined, concentrated to ~16.0 ml, kept (25° C.) for two days and cyclopenol separated out, forming white crystals. The supernatant was concentrated and yellowish crystals ($R_f$ 0.09 on TLC) were isolated and had a mass spectra resembling that of viridicatol. Proton nuclear magnetic resonance ($^1$HNMR) analyses of the isolated compactin showed the spectral characteristics of the authentic compactin. The pure acetonitrile, methanol, and hexane soluble fractions exhibited various spectra with low U. V. absorbances (at 220 nm) of 0.00,0.26, and 0.08, respectively. Since the transition energies [Páducz, B., *Int. Rev. Cytol.* 21, 91–128 (1967)] in this region were higher for acetonitrile than for hexane and/or methanol, it was chosen for dissolving each fraction in subsequent analyses. The UV spectrum for compactin in acetonitrile exhibited maxima at 238 nm, with two minor peaks at 230 and 246 nm providing evidence for the presence of a bicyclic diene chromophore in the molecule identical to those reported in the Merck Index [Meigs, et al., *Exp. Cell Research*, 219, 416–470 (1995)]. The relationship between the absorbance at 238 nm and acetonitrile containing various compactin levels $\mu g$ $ml^{-1}$ acetonitrile), yielded a very high correlation (0.9999) with 0.5 $\mu g$ compactin $ml^{-1}$ as the detection limit and 2.3% maximal error. In the extracts of the SWM, cyclopenin interfered with compactin and separation was necessary using two directional HPTLC and the percent recovery of compactin from the TLC plates was 48.5%±2.5. The U. V. absorbance spectra for cyclopenol (16.20 $\mu g$ $ml^{-1}$ acetonitrile) had only one maxima at 286 nm, thus confirming Cutler et al.[*Plan and Cell Physiol.*, 25, 257–263 (1984)] data. The absorbance at 286 mn of different cyclopenol levels ($\mu g$ $ml^{-1}$ acetonitrile) had a very high correlation (0.9999) in the range of 1.0–50yg cyclopenol $ml^{-1}$ acetonitrile and the detection limit was 1.0 $\mu g$ $ml^{-1}$ with 5.21% maximal error.

Factors Affecting Growth and Compactin Synthesis in Submerged Culture

Growth of P. cyclopium, (maximal density of 10.0 mg dry cells ml$^{-1}$) was noted after 10 days incubation in SYEMB with little changes thereafter. The levels of cell-masses in GBSB and in MGPB were not different, and were maximal after 8,6, and 10 days in MGPB, GBSB and in SYEMB, respectively. Growth in SYEMB was uniform possibly due to better contact between cells and nutrients leading to its higher transfer and cell-masses, accordingly. In the GBSB, growth was not uniform, and for MGPB it was in pelleted-form resulting in some limitations for nutrient transfer to the core of the pellets. The pH (of all media) changed from 5.5 to 3.3 within four days incubation and levels of the reducing sugars in SYEMB increased 2.5 fold, after 21 days, over that at zero time due to the high invertase activities of the mold. However, total carbohydrates (Table 1, below) decreased after 21 days to 30.0, 4.2 and 118.4 mg ml$^{-1}$ for MGPB, GBSB and SYEMB media, respectively. The SYEMB did not support compactin synthesis (Table 1) possibly due to hydrolysis of sucrsoe to glucose and fructose which in turn may have suppressed the production of enzyme(s) for compactin synthesis. The organism in MGPB showed enhanced compactin production to ~1.6 fold that of GBSB due to slow sugar utilization and the formation of pellets which stressed the organism and induced higher compactin synthesis (60.10 μg compactin ml) after 12 days. Drew and Wallis [*Fungi.*, Bennett and Ciegler, editors, pp. 35–54, 1983, Marcel Dekker New York]) reported that glucose often served as an excellent substrate for microbial growth, yet its rapid utilization and expression of secondary metabolites was found to be mutually exclusive in many cases. Thus, limiting glucose favors secondary metabolism by P. cyclopium, which did not sporulate during incubation in submerged culture as evidenced microscopically. Furthermore, cyclopenol and cyclopenin synthesis were completely suppressed (not detected in extracts), contrary to the data reported by Schroder, supra. Georgiou and Shuler [*Biotechnol. Bioeng.*, 28, 405416 (1986)] also stated that some conditions may be partially responsible for induction of differentiation, sporulation and secondary metabolites synthesis in solid-substrate fermentation with a define medium.

Increasing the air flow from 0.5 to 3.0 (v/v/min), decreased cell-mass in MGPB during 12 days incubation and enhanced collision between mycelia and hyphal tips thus, metabolism was directed toward the repair process rather than growth. Breakage of hyphal tips were detected microscopically at the air flow of 3.0 (v/v/min). Again the different aerations affected compactin production in MGPB under submerged cultural conditions and higher values were noted at 2 (v/v/min) as a function of incubation time (Table 2, below), and therefore this level of air flow was selected for all subsequent experiments. Again during growth of MGPB and in the absence of added glucose, the media had a total reducing sugar of 20.4 mg ml$^{-1}$ due to the presence of malt-extract, but in all treatments, cell-mass reached highest level after 8 days. Compactin production in the same media, but with different glucose levels (Table 3, below), increased and continued thereafter to the 12th day, especially in the presence of the low glucose level (1%). Unbuffered MGPB, with pH of 4.0,5.5 or 7.0, had no effect on cell-mass and compactin levels but the pH changed to 3.2 after two days incubation in all experiments. When the media were buffered by adding citrate or succinate (0.1M) to yield pH 4.0 or 5.5, good growth was noted at pH 4.0 compared to 5.5 and the stationary phase was reached after 4 and 6 days at pH 4.0 and 5.5, respectively. Mold sporulation was also initiated, on the 2nd and the 4th days at both pHs and the distinctive green color of the conidia was visible on the 5th day at pH 4.0, reaching maximal density on the 7th day (dark green). Sugar metabolism was limited during the 12 days at pH 4.0 compared to pH 5.5 and compactin levels also increased (Table 4, below), and therefore, citrate was added to MGPB (0.1 M, pH 4.0 ) in all further experiments.

TABLE 2

Effect if different aeration levels on compactin (comp) synthesis during incubation of P. cyclopium in MGPB under submerged conditions at 25° C.

| Incubation | Comp (μg ml$^{-1}$) ± SD and air levels (vv$^{-1}$ min$^{-1}$) | | |
|---|---|---|---|
| (days) | 0.5 | 2.0 | 3.0 |
| 2 | 0.00 | 0.00 | 0.00 |
| 4 | 15.72 ± 0.39 | 37.40 ± 0.50 | 12.11 ± 0.32 |

TABLE 1

Effect of Media on total Carbohydrate (CHO) profiles (anthrone reagen and on compactin (Comp) during growth (days, 25° C.) of P. cyclopium in submerged culture Total CHO (mg ml$^{-1}$) and comp (μg ml$^{-1}$) and comp (μg ml$^{-1}$) ± SD in:

| | MGPB | | GBSB | | SYEMB | |
|---|---|---|---|---|---|---|
| Incubation | CHO | Comp | CHO | Comp | CHO | Comp |
| 0 | 51.4 ± 1.9 | 0.00 | 89.4 ± 0.3 | 0.00 | 257.7 ± 8.0 | 0.0 |
| 2 | 48.7 ± 2.9 | 0.00 | 79.6 ± 0.6 | 0.00 | 234.4 ± 4.0 | 0.0 |
| 4 | 44.2 ± 1.0 | 29.80 ± 0.1 | 63.5 ± 1.8 | 10.56 ± 0.2 | 229.9 ± 7.8 | 0.0 |
| 6 | 40.4 ± 0.4 | 46.11 ± 0.2 | 53.6 ± 1.0 | 22.96 ± 0.7 | 210.2 ± 1.8 | 0.0 |
| 8 | 39.3 ± 1.0 | 54.21 ± 0.2 | 42.8 ± 1.0 | 30.91 ± 0.6 | 200.7 ± 2.7 | 0.0 |
| 10 | 37.2 ± 0.3 | 58.77 ± 0.1 | 33.7 ± 0.2 | 34.96 ± 0.5 | 190.2 ± 1.0 | 0.0 |
| 12 | 34.5 ± 1.0 | 60.10 ± 0.1 | 23.4 ± 0.5 | 37.75 ± 0.8 | 153.9 ± 4.3 | 0.0 |
| 15 | 31.4 ± 0.8 | ND[a] | 15.6 ± 0.6 | ND | 120.6 ± 1.4 | 0.0 |
| 18 | 30.1 ± 0.9 | ND | 7.6 ± 0.0 | ND | 120.3 ± 2.3 | 0.0 |
| 21 | 30.0 ± 1.0 | 60.11 ± 0.1 | 4.2 ± 0.0 | 38.02 ± 0.5 | 118.4 ± 1.0 | 0.0 |

[a]Not determined.

TABLE 2-continued

Effect if different aeration levels on compactin
(comp) synthesis during incubation of *P. cyclopium*
in MGPB under submerged conditions at 25° C.

| Incubation | Comp ($\mu$g ml$^{-1}$) ± SD and air levels (vv$^{-1}$ min$^{-1}$) | | |
|---|---|---|---|
| (days) | 0.5 | 2.0 | 3.0 |
| 6 | 37.61 ± 0.38 | 50.91 ± 0.25 | 34.92 ± 0.68 |
| 8 | 42.45 ± 0.42 | 60.11 ± 0.32 | 39.44 ± 0.51 |
| 10 | 45.01 ± 0.54 | 66.83 ± 0.43 | 41.25 ± 0.50 |
| 12 | 47.53 ± 0.81 | 70.00 ± 0.19 | 42.53 ± 0.41 |

TABLE 3

Effect of different glucose (glu) levels in MGPB on
compactin (comp) synthesis during growth of *P. cyclopium*
in submerged culture (25° C.)

| Incubation | Comp ($\mu$g ml$^{-1}$) ± SD at glu level (%) | | |
|---|---|---|---|
| (days) | 0.0 | 0.5 | 1.0 |
| 0 | 0.00 | 0.00 | 0.00 |
| 2 | 0.00 | 0.00 | 0.00 |
| 4 | 31.53 ± 0.83 | 39.18 ± 0.83 | 34.04 ± 0.57 |
| 6 | 46.22 ± 0.97 | 51.48 ± 0.94 | 55.01 ± 0.37 |
| 8 | 55.13 ± 1.34 | 63.54 ± 1.92 | 67.09 ± 1.13 |
| 10 | 58.06 ± 1.92 | 70.24 ± 1.12 | 74.12 ± 0.85 |
| 12 | 58.10 ± 0.56 | 73.31 ± 0.91 | 77.50 ± 1.33 |

TABLE 4

Effect of initial pH on compactin (comp) synthesis by
*P. cyclopium* during submered growth in MGPB
containing 0.1 M of citrate or succinate (pH 4.0) and succinate
(pH 5.5)

| | Comp ($\mu$g ml$^{-1}$) ± SD at initial pH | | |
|---|---|---|---|
| Incubation | pH 4.0 | | pH 5.5 |
| (days) | Citrate | Succinate | Succinate |
| 0 | 0.00 | 0.00 | 0.00 |
| 2 | 11.62 ± 0.22 | 0.00 | 0.00 |
| 4 | 35.41 ± 0.82 | 31.13 ± 0.72 | 39.98 ± 0.94 |
| 6 | 50.90 ± 0.93 | 59.28 ± 1.01 | 54.44 ± 0.83 |
| 8 | 67.51 ± 0.42 | 76.24 ± 2.15 | 65.03 ± 0.27 |
| 10 | 84.79 ± 1.40 | 82.94 ± 2.01 | 73.75 ± 0.77 |
| 12 | 93.49 ± 2.29 | 92.91 ± 2.41 | 74.07 ± 1.98 |

Schröder, supra, stated that the presence of citrate and Ca$^{++}$ stimulated sporulation and the synthesis of alkaloids by *P. cyclopium*. Under our experimental conditions, sporulation occurred during compactin synthesis in the citrate buffered MGPB, but no alkaloids were detected. Again, Schröder, supra reported that citrate played a key role in pH stabilization, metal chelation and suppression of glycolysis, possibly altering it to gluconeogenesis. Acetate, on the other hand, inhibited the *P. cyclopium* growth, whereas citrate and/or succinate supported it and more growth was achieved in MGPB contaning citrate reaching the stationary phase within four days incubation with slight changes thereafter to the 12th day. Slower growth was noted in the presence of succinate on the 8th day followed by a decline thereafter, possibly due to lysis of cells as noted microscopically. We believe that citrate was utilized faster during the 2nd to 4th day as compared to succinate leading to the rapid growth, enhance of cell specialization and sporulation. Sporulation was also initiated after two days in the presence of citrate and after four days in succinate. Maximal pigmentation was evident (visually) on the 6th day for the MGPB with citrate and on 12th day with succinate. During growth, the pH of MGPB changed but was more stable in media containing succinate possibly due to ammonia liberation during the deamination reactions. However, no statistical difference was observed between compactin levels in media containing citrate or succinate at pH 4.0 but not at pH 5.5 for succinate during 12 days incubation (Table 4, above). The molar concentrations of citrate in MGPB (buffered to pH 4.0 ) and under submerged conditions had no significant effects on cell-mass or sugar utilization.

The compactin synthesis reached higher level in 0.01 M citrate compared to either 0.05 or 0.1 M citrate (Table 5, below) even though the cell-mass was almost the same in MGPB containing either one of the three different molar citrate levels. Factors yielding maximal compactin synthesis in submerged culture (Table 6, below) indicated that both compactin formed (mg l$^{-1}$) and productivities (mg l$^{-1}$ d$^{-1}$) markedly increased and also showed that air flow, initial pH of MGPB with citrate [modified (B) media] as well as 0.01 M citrate lead to the higher level of compactin than the glucose (5.0 g l$^{-1}$) in modified (A) MGPB. Both aeration and glucose enhanced growth leading to slightly higher compactin level. However, both 0.01 M citrate and the low glucose level in the modified (B) MGPB contributed to the pronounced synthesis of compactin (118.48 mg l$^{-1}$) and its permeation rather than growth of the organism.

TABLE 5

Effect of different molar citrate levels in MGPB
(pH 4.0) on compactin (comp) synthesis by *P. cyclopium*
during growth in submerged culture (25° C.)

| Incubation | Comp ($\mu$g ml$^{-1}$) ± SD in media with citrate level (M) | | |
|---|---|---|---|
| (days) | 0.01 | 0.05 | 0.10 |
| 0 | 0.00 | 0.00 | 0.00 |
| 2 | 8.40 ± 0.38 | 0.00 | 11.62 ± 0.22 |
| 4 | 30.15 ± 1.26 | 31.18 ± 1.31 | 35.41 ± 0.82 |
| 6 | 48.27 ± 2.30 | 50.66 ± 2.05 | 50.90 ± 0.93 |
| 8 | 86.69 ± 1.71 | 65.00 ± 1.38 | 67.51 ± 0.41 |
| 10 | 110.27 ± 1.36 | 84.29 ± 2.14 | 84.79 ± 2.72 |
| 12 | 118.48 ± 0.82 | 94.11 ± 3.37 | 93.49 ± 2.29 |

TABLE 6

Factors affecting maximal compactin formation and
productivity by *P. cyclopium* during submerged growth
in MGPB modified media (A) and (B). Media compositions are
listed in Materials and Methods.

| | Compactin | |
|---|---|---|
| Factor examined | Formed (mg L$^{-1}$) | Productivity (mg L$^{-1}$ h$^{-1}$) |
| Air flow | | |
| 1 vv$^{-1}$ min$^{-1}$ | 60.05 | 5.00 |
| 2 vv$^{-1}$ min$^{-1}$ | 70.00 | 5.83 |
| Modified medium (A), glucose (5.0 gL$^{-1}$) | 73.31 | 6.11 |
| Modified medium (B), pH 4.0 | | |
| (0.10 M citrate) | 93.49 | 7.79 |
| (0.01 M citrate) | 118.48 | 9.87 |

Immobilization

The SEM of loofah sponge prior to immobilization showed the fiber network with different directional changes and internal pores as well as channels sizes. Longitudinal channnels were also noted on surfaces of the loofah fibers and the cross-section exhibited bundle of fibrils averaging 0.4 mm, and the individual fibrils were very porous with diameters ranging from 5 $\mu$m to 25 $\mu$m. When the loofah was inoculated, the condidiospores were firmly attached to the surface channels, averaging 3.5 $\mu$m in diameter with irregular rough surfaces. The initiation of spore germination on the loofah was detected within the first 10 h, followed by rapid growth with hypha branching as well as septa formation, and colonies were evident on the loofah surfaces within 24 h. The mycelia covered the entire loofah within 48–72 h with sporulation and maximal conidiospore pigmentation after 96 h incubation. The loofah had large, rough channeled surfaces aiding the attachments of the spores and hyphae. The large internal spaces of the loofah facilitated nutrient mass transfer, product synthesis and air movement during fermentation. Again, the loofah sponge is very light weight, durable with no apparent evidence of fiber hydrolysis following continuous (two months) operation of the immobilized system. The results for the morphological changes during the submerged growth of P. cyclopium in MGPB, or in the modified (B) MGPB media as well as in the shake-flask fermentation, and utilizing immobilized fungal preparations, showed the type of differentiation, the sporulation (48 h), pigmentation (72– 96 h) as well as three growth phases: lag (germination), log (trophophase) and stationary (idiophase) thus confiriming Luckneres [Luckner, *J. Nat. Prod.*, 43, 32–40 (1980)] observations.

Immobilized Batch.

At zero time, the initial cell-mass (inoculum) in the control (no loofah) and in the flasks containing the free-spore-cells immobilized on the loofah cubes were 0.71 and 0.61 mg dry wt ml$^{-1}$ broth, respectively (Table 7, below). The trophophase cells (36 h), used for immobilization, were in the log growth phase and resulted in rapid biomass increase (26.68 mg dry wt ml l$^{-1}$) within two days reaching maximal level, but with different magnitude, within 12 days in all experiments as indicated in the same table. We believe that the loofah cubes enhanced rapid fungal growth and provided protection for the hyphal tips during agitation collision and allowed for vigorous growth in the internal spaces of the loofah cubes. However, the mold-surface cells were completely damaged and exhibited abnormal ends due to collision of cubes and growth appeared toward the center of the loofah where the tips were protected. Idiophase-immobilized-cell-preparations (106 h) showed slight increase in cell-mass during growth (0–12 days) possibly due to presence of some metabolites in the inoculum. Different ages of inocula were also used in the modified (B) MGPB shake culture with free-spore-cells (control) and showed no significant difference in sugar uptake (%) during the first 6 days fermentation between control and free-spores as well as between trophophase (36 h) and idiophase (106 h) immobilized-cell-preparations. However, after the 6th day, the reducing sugar uptake decreased (but-not significantly) in both control and immobilized idiophase cells (data not shown). The level of compactin, during fermentation in shake culture, increased to maximal level at different intervals (days) for all experiments (Table 8, below). However, the highest value was noted in the control compared to all other treatments. The rapid production of compactin using the immobilized idiophase-cells during early growth (2–4 days) was probably due to its excretion into the media from the inoculum and possible synthesis thereafter. The control flasks with free-spore-cells in the modified (B) MGPB had higher compactin level than in other flasks containing the immobilized-cell preparations, possibly due to decrease in cells-mass and improved aeration. Cyclopenol was also detected in the immobilized idiophase cell preparations (probably present in spores) and excreted into media. Luckner, supra stated that cyclopenin, cyclopenol, viridicatin, and viridicatol were mostly synthesized in the conidiospores and excreted into broth due to changes in spore cell permeabilities.

TABLE 7

Cell mass (mg dry wt ml$^{-1}$) profiles for different ages of immobilized P. cyclopium cells dunng growth in modified (B) MGPB media with shaking at 25° C.. The control had free cells

| Incubation | Cell mass (mg ml$^{-1}$) and conditions | | | |
|---|---|---|---|---|
| (days) | Control | Free spores | 36 h | 106 h |
| 0 | 0.71 | 0.61 | 11.44 | 31.25 |
| 2 | 2.76 | 5.67 | 26.68 | 32.59 |
| 4 | 4.09 | 8.92 | 28.32 | 35.50 |
| 6 | 4.39 | 10.55 | 28.63 | 36.51 |
| 8 | 4.51 | 10.86 | 28.50 | 36.82 |
| 10 | 4.99 | 10.93 | 28.70 | 37.49 |
| 12 | 5.49 | 10.99 | 29.57 | 37.61 |

TABLE 8

Compactin (comp) synthesis using different growth phases for immobilization of P. cyclopium spores on loofah cubes using the modified (B) MGPB in shaken flasks and control had free cells (non-immobilized)

| Incubation | Comp ($\mu$g ml$^{-1}$) ± SD and growth phase | | | |
|---|---|---|---|---|
| time (days) | Control | Free spores | Trophosphase (36 h) | Idiophase (106 h) |
| 0 | 0.00 | 0.00 | 0.00 | 0.00 |
| 2 | 23.51 ± 1.32 | 17.73 ± 1.31 | 19.71 ± 0.66 | 42.70 ± 2.34 |
| 4 | 61.81 ± 2.33 | 47.34 ± 2.45 | 34.24 ± 0.27 | 48.56 ± 2.85 |
| 6 | 84.73 ± 1.42 | 56.40 ± 2.25 | 49.32 ± 1.08 | 111.83 ± 3.34 |
| 8 | 112.90 ± 5.19 | 80.62 ± 2.62 | 77.95 ± 1.84 | 100.87 ± 3.60 |
| 10 | 130.01 ± 2.71 | 92.11 ± 2.63 | 108.33 ± 4.86 | 111.91 ± 3.55 |
| 12 | 157.85 ± 1.90 | 105.00 ± 1.44 | 111.00 ± 0.86 | 112.50 ± 2.14 |
| 14 | 170.05 ± 1.71 | 106.02 ± 1.83 | 111.07 ± 1.11 | 112.61 ± 1.96 | loofah cubes per flask, the more the cell-mass formed due to increased surface area for spore attachment, germination and growth. The highest specific compactin concentration (38.4 mg compactin g$^{-1}$ dry loofah sponge) was noted when free-cells (control) were used. The continuous system with loofah cubes (column I) using modified (B) MGPB media resulted in many operational problems after the 5th day of static fermentation due to blocking by mold growth both air movement and nutrients into the column. Therefore, the larger column II, containing the entire loofah sponge, was subsequently used. An inproved mass transfer of both air and nutrients during operations of the bioreactor with column II was observed. The bioreactor system was kept static for seven days (batch-fermentation system without added FS) and on the 7th day, compactin level was 78.6 $\mu$g ml l$^{-1}$ broth and remained constant on the 8th and 9th day (77.9 and 77.5/$\mu$g ml$^{-1}$), respectively When the feedstock [modified (B) MGPB] was continuously fed (pumped) to the system, at various dilution rates (flow rates of 7.8 to 90.0 ml h$^{-1}$), the results (Table 10) indicated that higher dilution rates (0.12 to 1.35 d$^{-1}$) changed the pH (from 3.3 to 4.0) and reducing sugar levels from 10.6 to 19.6 mg glucose equivalent ml$^{-1}$, respectively. The compactin productivities (mg l$^{-1}$ d$^{-1}$) reached 23.04 at a dilution rate of 0.45 d$^{-1}$ (30 ml h$^{-1}$ flow rate) on both the 4.44 days and thereafter to the 30th day. However, compactin productivities declined to 13.82 mgl$^{-1}$ d$^{-1}$ at dilution rate of 1.35 d$^{-1}$ (90 ml h$^{-1}$ flow rate) on the 33rd and 34th day, respectively. This decline was mostly due to the rapid flow of the FS and after 34 days of operation, the FS dilution rate was then reduced to 0.45 d$^{-1}$ and the productivities, during the 36th to the 50th day, were constant (23.04 mg l$^{-1}$ d$^{-1}$). The bioreactor system was operated continuously to the 51st day and turned off thereafter due to the massive fingal growth and to limited air supply as well as nutrient transfer, leading to the plugging effect. These results showed that the immobilized *P. cyclopium*, in a continuous bioreactor system, improved the productivities over that noted for the submerged culture with air sparget. Application of immobilized microorganisms and carder support used for the production of various secondary metabolites are of interest and have been reported by several investigators [Tsumita, et al., *Biochem. Biophys. Acta*., 877, 50–60 (1986); Chung, et al, *Biotechnol. Bioeng*., 32, 205–212 (1988); Tamada, et al., *Biotechnol. Bioeng*., 28, 1227–1232 (1969); Larroche, et al., *Biotechnol. Bioeng*., 34, 30–38 (1989); Saucedo, et al. *Appl. Environ. Microbiol*., 55. 2477–2384 (1989); Endo, et al., *Bioprocess Eng*., 3, 63–68 (1988); and O'Reilly, et al., *Appl. Environ. Microbiol*. 55, 2113–2118 (1989)], polyurethane [Saucedo, et al., *Appl. Environ. Microbiol*., 55. 2477–2384 (1989); Endo, et al., *Bioprocess Eng*., 3, 63–68 (1988); and O'Reilly, et-al., *Appl. Environ. Microbiol*. 55, 2113–2118 (1989)], non-woven materials [Tamada, et al., *Biotechnol. Bioeng*., 28, 1227–1232 (1969)], and carrageenan [, et al.,*Appl. Environ. Microbiol*., 55. 2477–2384 (1989)]. Again, Saucedo et al. [*Appl. Environ. Microbiol*., 55. 2477–2384 (1989)] stated that factors such as type of carrier, inoculum size, type of inoculum [spores or vegetative cells (mycelia)] and culture conditions (static, agitated or continuous) might lead to different fungal behaviors and as a result, different data might be obtained. Some authors reported lower productivities using the reactor system than that using the conventional system and this is probably due to some limitations in mass transfer of substrate, product, oxygen, and dilution rate [Kim, et al., *Biotechnol. Bioeng*., 28, 1834–1844 (1986); Dawson, et al., *Biotechnol. Bioeng*., 32, 220–226 (1988); and San, et al., *Biotechnol. Bioeng*., 34, 72–78 (1989)]. Therefore, new, effective immobilization methods for improving the efficiency of mass transfer and productivities will be of interest. In the present investigation the use of loofah sponge was evaluated as a novel carrier support for fungal cells and resulted in higher compactin yield. The loofah is the fruit of the plant *Luffa aegyptiaca* from the Cucurbitaceae family [Muschler, supra.]. Dried loofah has a fibrous, semi-rigid, sponge-like interior and is usually used as a gentle, abrasive washing sponge.

Kinetics of Product Formation.

Monod constant values of compactin synthesis in the submerged culture using modified (A) MGPB culture (air sparget, shake flask and trophophase immobilized-cells) were calculated and the results were 60.0,91.7 and 82.0, respectively. These values were somewhat high compared to values reported for primary metabolite production and are probably due to the fact that the precursor of compactin is not known at present. Microbial growth is a complex phenomenon but the overall growth can often be regarded as a single chemical reaction with a simple rate expression. One of the simplest and most popular equations by Monod, supra was used for analyzing kinetics of fermentation, and for cell mass as primary metabolite production. Secondary metabolite synthesis also fitted the Monod model but to a different magnitude from those previously for the former analyses.

It is to be understood by those skilled in the art that the foregoing description and examples are illustrative of practicing the present invention, but are in no way limiting. Variations of the detail presented herein may be made without departing from the spirit and scope of the present invention as defined by the following claims.

What is claimed is:

1. An immobilized natural product producing fungi for use in the production of a natural product comprising spores of a natural product producing fungi immobilized into or onto loofah sponge.

2. The immobilized fungi according to claim 1 wherein said fungi is *Penicillium cyclopium*.

3. The immobilized fungi according to claim 1 wherein said fungi is *Penicillium cyclopium* NRRL 6233.

4. A method of synthesizing a natural product from fungi comprising the steps of:
   i) immobilizing spores of a natual product producing fungi into or onto an immobilizing support selected from the group consisting of loofah sponge, synthetic sponge, powdered cellulose paper, wood shavings, calcium alginate gel beads, agar gel beads, channelled aluminum beads, polypropylene beads and glass beads to produce immobilized spores;
   ii) exposing said immobilized spores from step i) to nutrient media for a period of at least 4 days to produce a fermented media containing a natural product metabolite of said fungi; and
   iii) collecting said fermented media and isolating said natural product from said fermented media.

5. The method according to claim 4 wherein said fungi is selected from the group consisting of *Penicillium cyclopium, Penicillium chrysogenum, Penicillium citrinum, Trichoderma viride, Aspergillus terreus* and *Monascus Tuber.*

6. The method according to claim 5 wherein said natural product is an antibiotic.

7. The method according to claim 4 wherein said natural product is a growth regulator.

8. The method according to claim 4 wherein said immobilizing support is loofah sponge.

9. The method according to claim 4 wherein said immobilizing support is selected from the group consisting of synthetic sponge, powdered cellulose paper and wood shavings.

10. The method according to claim 4 wherein said natural product is selected from the group consisting of an antibiotic, an anti-fimgal agent and a growth regulator.

11. The method according to claim 4 wherein said collecting step is performed continuously.

12. A method of synthesizing compactin from the fungi *Penicillium cyclopium* comprising the steps of:
   i) immobilizing spores of said fungi into or onto an immobilizing support selected from the group consisting of loofah sponge, synthetic sponge, powdered cellulose paper, wood shavings, calcium alginate gel beads, agar gel beads, channelled aluminum beads, polypropylene beads and glass beads to produce immobilized spores;
   ii) exposing said immobilized spores from step i) to nutrient media for a period of at least 4 days to produce a fermented media containing compactint; and
   iii) collecting said fermented media and isolating said compactin from said fermented media.

13. The method according to claim 12 wherein said media contains a buffer and is adjusted to a pH ranging from about 4.0 to about 5.5.

14. The method according to claim 12 wherein said nutrient media is malt glucose peptone broth.

15. The method according to claim 12 wherein said fungi is *Penicillium cyclopium* NRRL 6233.

16. The method according to claim 12 wherein said immobilizing support is loofah sponge.

17. The method according to claim 12 wherein said immobilizing support is selected from the group consisting of synthetic sponge, powdered cellulose paper and wood shavings.

18. The method according to claim 12 wherein said collecting step is performed continuously.

19. The method according to claim 12 wherein said media is malt glucose peptone broth wbich contains a buffer and is adjused to pH of about 4.0 to about 5.5, said support is loofah sponge and said fungi is *Penicillium cyclopium* NRRL 6233.

* * * * *